United States Patent
Jor

(10) Patent No.: US 11,273,242 B2
(45) Date of Patent: Mar. 15, 2022

(54) BACKFLOW PREVENTION DEVICE AND DIALYSIS APPARATUS WITH THE BACKFLOW PREVENTION DEVICE

(71) Applicant: Fresenius Medical Care Deutschland GmbH, Bad Homburg (DE)

(72) Inventor: Joseph Jor, Hong Kong (CN)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/956,329

(22) PCT Filed: Dec. 22, 2017

(86) PCT No.: PCT/CN2017/117991
§ 371 (c)(1),
(2) Date: Jun. 19, 2020

(87) PCT Pub. No.: WO2019/119414
PCT Pub. Date: Jun. 27, 2019

(65) Prior Publication Data
US 2021/0077695 A1      Mar. 18, 2021

(51) Int. Cl.
*G05D 11/00* (2006.01)
*A61M 1/16* (2006.01)
(Continued)

(52) U.S. Cl.
CPC .......... *A61M 1/1621* (2014.02); *A61M 39/24* (2013.01); *F16K 15/028* (2013.01);
(Continued)

(58) Field of Classification Search
CPC ......... Y10T 137/7787; Y10T 137/2645; Y10T 137/2642; Y10T 137/2663; A61M 1/1601
See application file for complete search history.

(56) References Cited

U.S. PATENT DOCUMENTS

| 3,818,929 A | 6/1974 | Braukmann |
| 4,948,092 A | 8/1990 | Kasper et al. |

(Continued)

FOREIGN PATENT DOCUMENTS

| CN | 101936412 | 1/2011 |
| CN | 102252116 | 11/2011 |

(Continued)

OTHER PUBLICATIONS

PCT International Preliminary Report on Patentability in Application No. PCT/CN2017/117991, dated Jun. 23, 2020, 4 pages.

(Continued)

*Primary Examiner* — Robert K Arundale
(74) *Attorney, Agent, or Firm* — Fish & Richardson P.C.

(57) ABSTRACT

The present disclosure provides a backflow prevention device, comprising: an inlet chamber comprising at least two ports, in which a first port is used for receiving a fluid; a chamber-separating component comprising a separating member and a relief valve; an outlet chamber separated from the inlet chamber by the separating member; the relief valve being operatively connected with the separating member for opening or closing a drain port of the outlet chamber; wherein the fluid is allowed to be delivered from the outlet chamber only when the relief valve is closed by means of a differential pressure applied on the separating member. Also provided is a dialysis apparatus comprising the backflow prevention device. According to the present disclosure, the backflow prevention device has simple structure, reduced dead space and small sizes and can work reliably.

20 Claims, 3 Drawing Sheets

(51) Int. Cl.
*A61M 39/24* (2006.01)
*F16K 15/02* (2006.01)
*F16K 17/04* (2006.01)
*F16K 31/126* (2006.01)

(52) U.S. Cl.
CPC .......... *F16K 17/04* (2013.01); *F16K 17/0473* (2013.01); *F16K 31/1262* (2013.01); *F16K 31/1266* (2013.01); *A61M 1/1601* (2014.02); *A61M 2205/15* (2013.01); *A61M 2209/10* (2013.01); *F16K 17/048* (2013.01); *Y10T 137/2645* (2015.04)

(56) References Cited

U.S. PATENT DOCUMENTS

2008/0216898 A1* 9/2008 Grant .................. A61M 60/268
137/154
2010/0192686 A1* 8/2010 Kamen ............... A61M 1/1601
73/290 R
2011/0108482 A1 5/2011 Lovell

FOREIGN PATENT DOCUMENTS

| | | |
|---|---|---|
| CN | 202397973 | 8/2012 |
| CN | 105363086 | 3/2016 |
| EP | 1027901 | 8/2000 |
| JP | 2866874 | 3/1999 |

OTHER PUBLICATIONS

PCT International Search Report and Written Opinion in Application No. PCT/CN2017/117991, dated Sep. 14, 2018, 7 pages.
EP Extended European Search Report in European Appln. No. 17935147.3, dated Jul. 30, 2021, 7 pages.

* cited by examiner

BACKFLOW PREVENTION DEVICE AND DIALYSIS APPARATUS WITH THE BACKFLOW PREVENTION DEVICE

CROSS-REFERENCE TO RELATED APPLICATIONS

The present application is the national stage entry of International Patent Application No. PCT/CN2017/117991, filed on Dec. 22, 2017, the disclosures of which is expressly incorporated herein in its entirety by reference thereto.

TECHNICAL FIELD

The present disclosure relates to a backflow prevention device for medical care purpose and a dialysis apparatus comprising the backflow prevention device.

BACKGROUND

A backflow prevention device is usually disposed between a fluid supply and a connected apparatus for receiving fluid from the fluid supply in order to protect the fluid supply from being contaminated or polluted by the connected apparatus.

Air gap separation method is a common means for preventing a backflow contamination risk. However, the air gap separation method can not be used in some applications, such as a pressurized operation.

In this case, a check valve or double-check valve backflow preventer is a basic form of a backflow prevention device. However, such a backflow preventer is not reliable because the valves may be incompletely closed due to particles or debris in a fluid pipeline; sometime the malfunction of the valves can not be completely avoided, either.

In some important applications, more sophisticated devices with redundancies, such as a reduced-pressure zone (RTZ) device is used. However, most RTZ devices available in the market are mainly produced for a portable water supply and are not suitable for a medical device due to the following reasons:

1) Most RTZ devices have internal flow paths that are not easily disinfected. Such devices have atmospheric vents and test valves that can introduce bacteria into distribution lines. Bacteria can colonize the device and re-contaminate the treated fluid, thereby causing harm to the patient if the device is used in a medical apparatus.

2) Chemical disinfectants may be trapped in the internal flow paths of the conventional RTZ devices during routine disinfection. The trapped disinfectants may then be released into the treated fluid, for example the reverse osmosis water during a dialysis treatment, thereby exposing the patient to a risk of toxicity of the disinfectants.

3) Most RTZ devices are constructed of materials which are not suitable for use with the medical device. Certain metals can contaminate the fluid and present a hazard to the patient.

SUMMARY OF THE DISCLOSURE

In view of the problems existing in the prior art, an object of the present disclosure is to provide an improved backflow prevention device and a dialysis apparatus comprising the backflow prevention device.

For achieving this object, according to a first aspect, provided is a backflow prevention device, comprising: an inlet chamber comprising at least two ports, in which a first port is used for receiving a fluid; a chamber-separating component comprising a separating member and a relief valve; an outlet chamber is separated from the inlet chamber by the separating member; the relief valve being operatively connected with the separating member for opening or closing a drain port of the outlet chamber; wherein the fluid is allowed to be delivered from the outlet chamber only when the relief valve is closed by means of a differential pressure applied on the separating member.

According to an optional embodiment, a second port of the inlet chamber is fluidly connected with a spring-loaded inlet check valve for delivering the fluid flowing across the inlet chamber from the first port.

According to an optional embodiment, the differential pressure is created by the spring-loaded inlet check valve which creates a pressure difference across the separating member when the fluid enters the inlet chamber.

According to an optional embodiment, a second port of the inlet chamber is fluidly connected with a differential pressure generator and an inlet check valve for delivering the fluid flowing across the inlet chamber from the first port.

According to an optional embodiment, the differential pressure is created by the differential pressure generator which creates a pressure difference across the separating member when the fluid enters the inlet chamber.

According to an optional embodiment, the inlet check valve is fluidly connected between the inlet chamber and the outlet chamber to only allow the fluid to flow from the inlet chamber toward the outlet chamber along a forward flowing path of the fluid.

According to an optional embodiment, the backflow prevention device further comprises: an outlet check valve being fluidly connected to the outlet chamber to only allow the fluid to flow through the outlet check valve for delivering the fluid from the outlet chamber, optionally, the outlet check valve being spring-loaded.

According to an optional embodiment, the backflow prevention device further comprises: a drain port cleaning valve for rinsing and/or disinfecting the drain port, which is fluidly connected between the inlet chamber and the outlet chamber in parallel with either a spring-loaded inlet check valve or a combination of an inlet check valve and a differential pressure generator serially connected with the inlet check valve.

According to an optional embodiment, the drain port is used for draining the fluid in the outlet chamber as a backflow prevention measure when there is a leak in an inflow path to the outlet chamber and/or a leak in a delivering flow path from the outlet chamber.

According to an optional embodiment, the separating member is configured as a flexible membrane, optionally, configured with a circular shape.

According to an optional embodiment, the chamber-separating component is supported by a support portion which extends inward radially from a corresponding inner wall of the backflow prevention device.

According to an optional embodiment, the relief valve is configured as a relief valve plunger connected with the separating member to form an integral assembly.

According to an optional embodiment, the assembly is supported by a spring which is supported on a bottom wall of the outlet chamber, optionally, the spring is a coil spring and surrounds the relief valve plunger.

According to an optional embodiment, the backflow prevention device further comprises: an inflow detecting means for detecting a leak in the drain port when there is no fluid consumption delivered in a fourth port from the outlet chamber while there is fluid flowing through an inflow path to the outlet chamber. Optionally, the inflow detecting means comprises a pair of electrodes disposed across an electrically insulated inlet check valve disposed in the inflow path.

According to an optional embodiment, the inlet chamber is configured above the outlet chamber, optionally each chamber is formed in a cylindrical body.

According to an optional embodiment, the outlet chamber has at least two ports, in which a third port is fluidly connected with an outlet of an inlet check valve fluidly disposed between the inlet chamber and the outlet chamber and a fourth port is fluidly connected with an inlet of an outlet check valve for delivering the fluid from the outlet chamber.

According to an optional embodiment, the relief valve plunger has a rod portion and a sealing head portion having a larger diameter compared with the rod portion, optionally, both the rod portion and the sealing head portion are integrated with the separating member and/or molded in one piece.

According to an optional embodiment, the drain port is centrally formed in the bottom wall of the outlet chamber; and/or the drain port is fluidly connected with a funnel drainpipe for air gap separation.

According to an optional embodiment, at least portions of the backflow prevention device contacting the fluid are formed from a biocompatible material.

According to an optional embodiment, the inlet chamber and/or the outlet chamber has a cylindrical cavity whose height is smaller than its radius respectively.

According to a second aspect, provided is a dialysis apparatus comprising the backflow prevention device.

According to the present disclosure, the backflow prevention device has simple structure, reduced dead space and small sizes and can work reliably.

BRIEF DESCRIPTION OF THE DRAWINGS

The present disclosure and advantages thereof will be further understood by reading the following detailed description of some preferred exemplary embodiments with reference to the drawings in which.

DETAILED DESCRIPTION OF EMBODIMENTS

Some exemplary embodiments of the present disclosure will be described hereinafter in more details with reference to the drawings to better understand the basic concept of the present disclosure.

Figure 1:
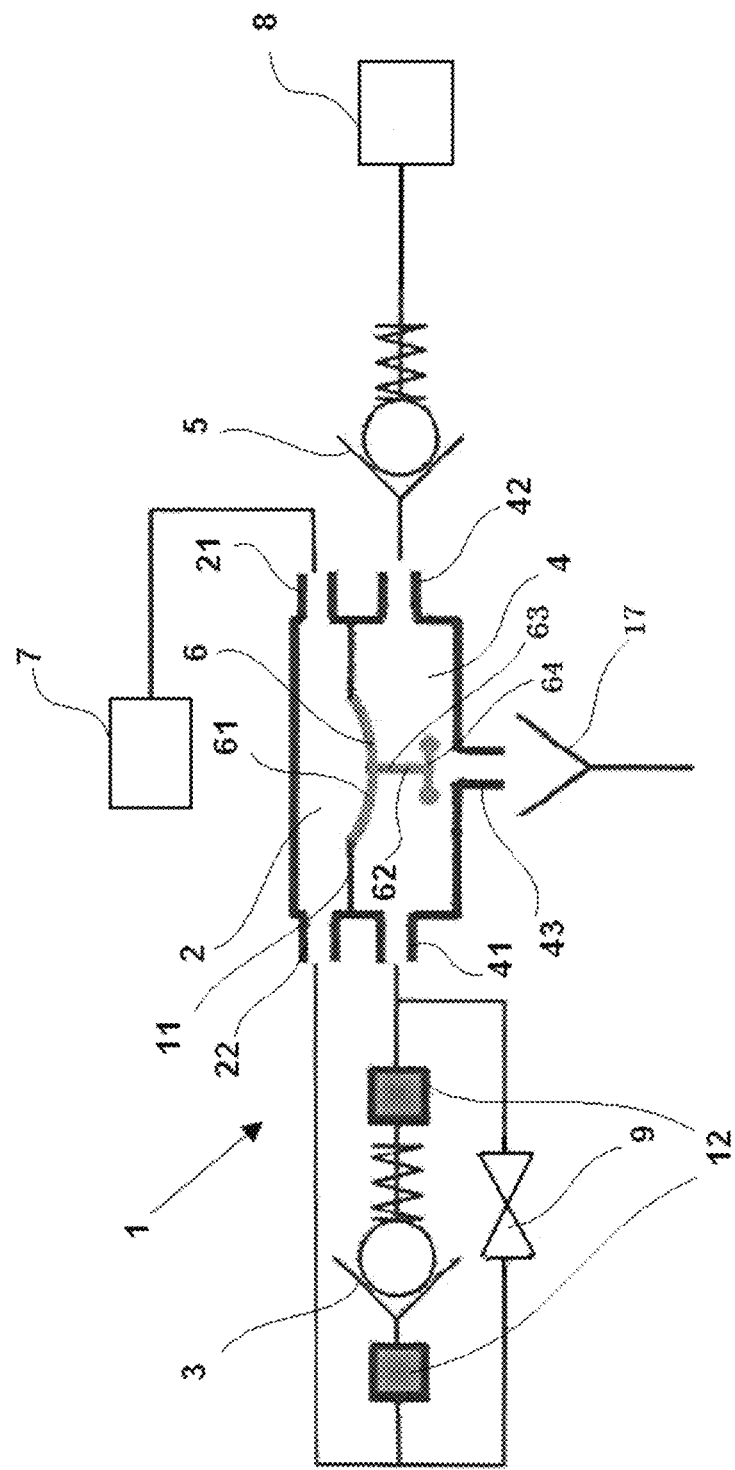
FIG. 1 shows a schematic sectional view of a backflow prevention device according to an exemplary embodiment of the present disclosure.

FIG. 1 shows a schematic sectional view of a backflow prevention device 1 according to an exemplary embodiment of the present disclosure.

As shown in FIG. 1, the backflow prevention device 1 mainly comprises: an inlet chamber 2 having a first port 21 and a second port 22, an inlet check valve 3 which is spring-loaded, an outlet chamber 4 having a third port 41, a fourth port 42 and a drain port 43, an outlet check valve 5 which preferably is spring-loaded, and a chamber-separating component 6, wherein the inlet chamber 2 is used for receiving fluid from a fluid supply 7 via the first port 21, the inlet check valve 3 is fluidly connected between the second port 22 and the third port 41 to only allow the fluid to flow from the inlet chamber 2 to the outlet chamber 4, the fourth port 42 of the outlet chamber 4 is fluidly connected with the outlet check valve 5 which is fluidly connected with an apparatus 8 requiring the fluid and only allows the fluid to flow from the fourth port 42 to the apparatus 8, and the chamber-separating component 6 comprises a separating member 61 separating the inlet chamber 2 from the outlet chamber 4 and a relief valve 62 connected with the separating member 61 and located within the outlet chamber 4. In operation, the relief valve 62 can move toward the drain port 43 to seal the drain port 43 by means of movement or elastic deformation of the separating member 61 when sufficient differential pressure is created by the spring-loaded inlet check valve 3. Although the drain port 43 may act as a valve seat in operation, the term "relief valve" does not include the drain port 43 in the context of the present application. In an initial state, the relief valve 62 is spaced from the drain port 43 so as to keep the drain port 43 open.

As further shown in FIG. 1, the relief valve 62 is preferably configured as a relief valve plunger connected with the separating member 61 to form an integral assembly.

According to an exemplary embodiment of the present disclosure, the fluid may be dialysate or reverse osmosis water. In this case, the apparatus may be a dialysis apparatus for dialysis treatment.

According to an exemplary embodiment of the present disclosure, the separating member 61 may be configured as a flexible membrane which is preferably integrated with the relief valve plunger, thereby achieving a simple structure design.

According to an exemplary embodiment of the present disclosure, as shown in FIG. 1, the relief valve plunger has a rod portion 63 and a sealing head portion 64 having a larger diameter compared with the rod portion 63. The rod portion 63 and the sealing head portion 64 are integrated with the separating member 61 from the same material and/or molded in one piece for small flow applications. In operation, the sealing head portion 64 is used for sealing the drain port 43.

According to an exemplary embodiment of the present disclosure, as shown in FIG. 1, the inlet chamber 2 and the outlet chamber 4 may be aligned one over the other.

Figure 2:
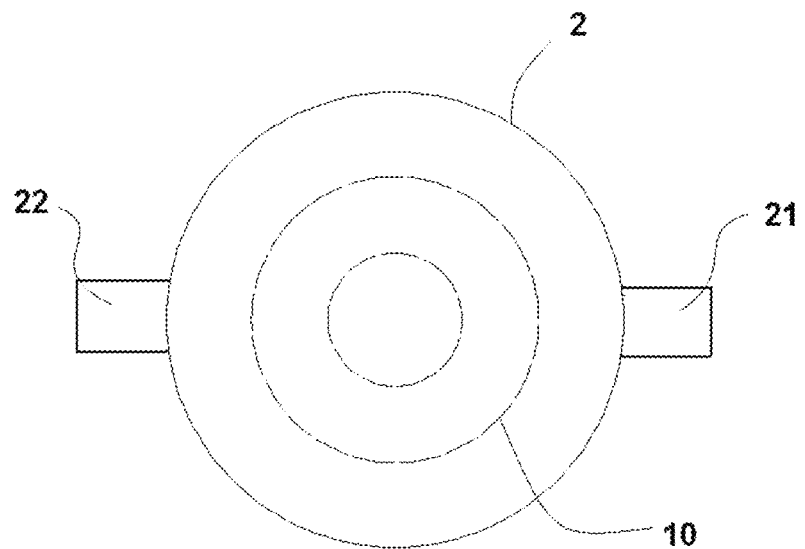
FIG. 2 shows a top view of a portion of the backflow prevention device as shown in FIG. 1.

FIG. 2 shows a top view of a portion of the backflow prevention device 1 as shown in FIG. 1.

Preferably, as shown in FIG. 1 and FIG. 2, both the inlet chamber 2 and the outlet chamber 4 each have a cylindrical body having the same diameter.

According to a further exemplary embodiment of the present disclosure, as shown in FIG. 1, the first port 21 and the second port 22 may extend outward diametrically from the cylindrical body of the inlet chamber 2, and/or the third port 41 and the fourth port 42 may extend outward diametrically from the cylindrical body of the outlet chamber 4, and/or the drain port 43 may extend downward centrically from a bottom wall of the outlet chamber 4. With such an arrangement, flow resistance of the backflow prevention device can be reduced, a compact design can be achieved, and the interior space of the inlet chamber 2 and/or the outlet chamber 4 can be cleaned and/or disinfected easily.

Preferably, in an assembled state, the first port 21 and the fourth port 42 are oriented in the first same direction such that they overlap from the top view of the backflow prevention device 1. Similarly, the second port 22 and the third port 41 are oriented in the second same direction opposite to the first same direction in the assembled state. With such an arrangement, the backflow prevention device 1 may have a trim appearance.

As further shown in FIG. 1, the drain port 43 can be used in the open state to drain the fluid from the outlet chamber 4 to any suitable means, such as a receptacle (not shown). For further preventing contamination from the drain port 43, the drain port 43 is connected with a funnel drainpipe 17 for air-gap separation.

According to an exemplary embodiment of the present disclosure, a drain port cleaning valve 9 is fluidly connected between the inlet chamber 2 and the outlet chamber 4 in parallel with the spring-loaded inlet check valve 3 or optionally an inlet check valve with a differential pressure generator connected in series such that if the drain port cleaning valve 9 is opened to equalize pressure across the separating member 61, the fluid can then be guided from the fluid supply 7 to the drain port 43 via the inlet chamber 2, the opened drain port cleaning valve 9 and the outlet chamber 4. Accordingly, the drain port 43 can be rinsed by the fluid from the fluid supply 7. With the drain port cleaning valve 9, the drain port 43 also can be disinfected by using any suitable fluid.

According to an exemplary embodiment of the present disclosure, the separating member 61 has a circular shape and is disposed aligned with the drain port 43. In FIG. 2, the separating member 61 is shown in a dashed 10.

As shown in FIG. 1, the separating member 61 may be supported circumferentially at a support portion 11 which extends inward radially from a corresponding inner wall of the backflow prevention device 1.

According to an exemplary embodiment of the present disclosure, an inflow detection means is provided to detect if the fluid flows through the inlet check valve 3. Preferably, the inflow detection means comprises a pair of inflow detection electrodes 12 disposed across the inlet check valve 3 which is electrically insulated. When the fluid is flowing through the inlet check valve 3, the conductivity between the pair of electrodes 12 becomes high. In addition, the inflow detection means can be used to detect if there is a leak in the relief valve, which will be further described below.

Figure 3:
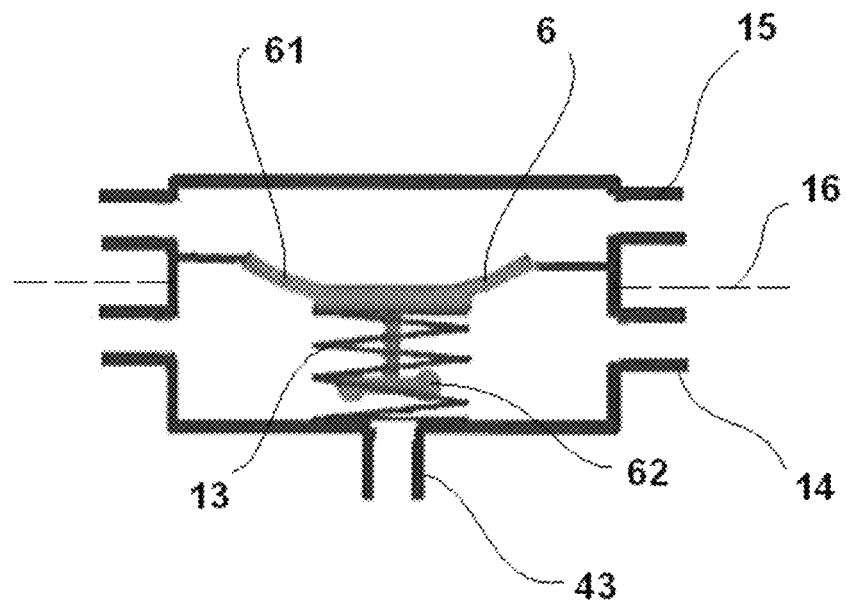
FIG. 3 shows a schematic sectional view of a portion of a backflow prevention device especially suitable for high flow applications, according to another exemplary embodiment of the present disclosure.

FIG. 3 shows a schematic sectional view of a portion of a backflow prevention device especially suitable for high flow applications, according to another exemplary embodiment of the present disclosure.

As shown in FIG. 3, the chamber-separating component 6 may be supported by a spring 13, preferably a coil spring. The spring 13 may be provided around the relief valve plunger and may be supported by a portion of the bottom wall of the outlet chamber 4 surrounding the drain port 43. In this way, the spring 13 could always make the relief valve plunger stable and be placed in the right position for completely closing the drain port 43.

For facilitating assembly of the backflow prevention device 1 and simplifying structure of the backflow prevention device 1, the backflow prevention device 1 may comprise a first part 14 and a second part 15 which can be fitted together along a fitting plane 16 which are only schematically shown in FIG. 3. Preferably, a sealing means, such as O-ring or the elastic separating member itself is provided between the first part 14 and the second part 15. According to an exemplary embodiment of the present disclosure, the first part 14 and the second part 15 are fitted together by means of screws or other fixation means (not shown).

According to an exemplary embodiment of the present disclosure, the first part 14 at least comprises the inlet chamber 2 and the chamber-separating component 6, and the second part 15 at least comprises the outlet chamber 4 and the drain port 43.

For dialysis application, at least portions of the backflow prevention device 1 contacting the fluid are formed from biocompatible materials which can withstand heat and chemical disinfection. The biocompatible material may for example be parylene, glutin, nitrocellulose and so on.

The inventive backflow prevention device 1 may be configured such that the inlet chamber 2 and/or outlet chamber 4 has smooth-profiled interior shape and reduced dead space, in particular in the case of the above described cylindrical bodies of the inlet chamber 2 and/or outlet chamber 4.

According to an exemplary embodiment of the present disclosure, the inlet chamber 2 and/or the outlet chamber 4 may be configured to have compact design with minimal chamber volume to ensure sufficient fluid flow along interior surface of the chamber(s) to avoid biological problem. For example, the inlet chamber 2 and/or the outlet chamber 4 may be configured to have a cylindrical cavity whose height is smaller than its radius respectively.

Below, an operation process of the backflow prevention device 1 will be described in detail.

The inventive backflow prevention device 1 operates based on the hydraulic principle that the fluid will not flow from a zone of lower pressure to a zone of higher pressure. As a differential pressure can be created by the spring-loaded inlet check valve 3, the relief valve 62 will be held in a closed position when a pressure of the fluid supplied into the inlet chamber 2 is higher by a predetermined amount than that in the outlet chamber 4, and then if the pressure in the inlet chamber 2 increases to a level enough to open the inlet check valve 3, the fluid will flow into the outlet chamber 4 and further open the outlet check valve 5. When the pressure in the inlet chamber 2 falls below a set value, the relief valve 62 will be opened and then the fluid in the outlet chamber 4 will be drained via the drain port 43. If the pressure in the outlet chamber 4 is enough to open the relief valve 62 and/or a fault exists in the outlet check valve 5, the fluid in the outlet chamber 4 also will be drained via the drain port 43.

If there is a leak in the inlet check valve 3, the pressures in the inlet chamber 2 and the outlet chamber 4 will become equalized, the relief valve 62 will be opened to divert the backflow fluid to the drain port 43.

If there is a leak in the outlet check valve 5, the backflow fluid will first be blocked by the inlet check valve 3. When the backflow fluid pressure reaches to a certain value, the relief valve 62 will be opened to divert the backflow fluid to the drain port 43.

If there are leaks in both the inlet check valve 3 and the outlet check valve 5, the relief valve 62 also will be opened to divert the backflow fluid to the drain port 43.

If there is a leak in the relief valve 62, it can be detected in a cutoff state of a downstream flow path (not shown) of the backflow prevention device 1 by detecting if the fluid flows through the inlet check valve 3, for example by measuring the conductivity between the pair of electrodes 12. If the fluid still flows through the inlet check valve 3 in this state, the leak may exist in the relief valve 62.

Figure 4:
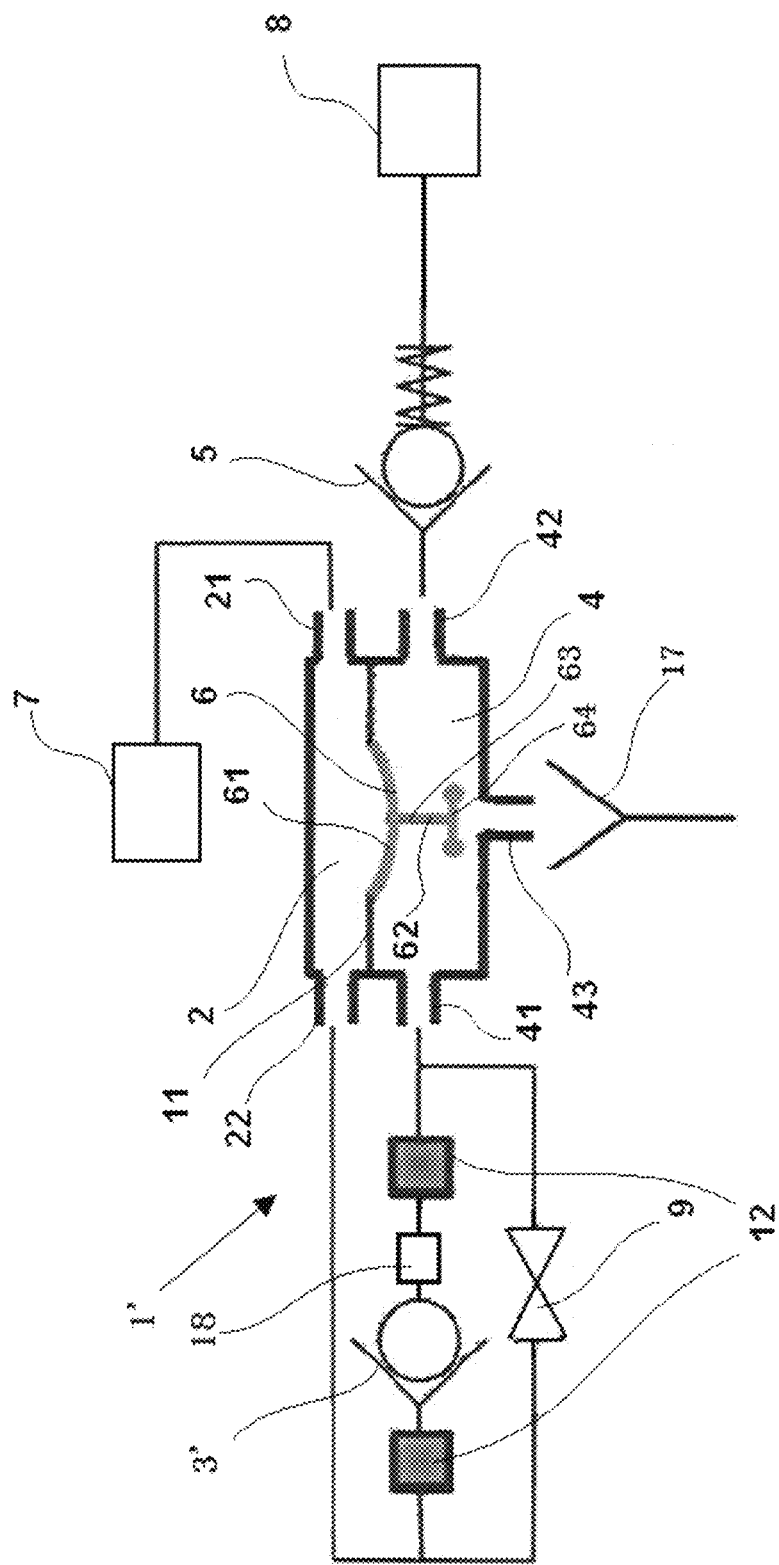
FIG. 4 shows a schematic sectional view of a backflow prevention device according to another exemplary embodiment of the present disclosure.

It should be understood by a skilled person in the art that the differential pressure also may be created in other manner, for example by using a separate differential pressure generator. FIG. 4 shows a schematic sectional view of a backflow prevention device 1' according to another exemplary embodiment of the present disclosure.

As shown in FIG. 4, the backflow prevention device 1' differs from the backflow prevention device 1 only in that a combination of an inlet check valve 3' and a differential pressure generator 18 serially with the inlet check valve 3' is used to replace the spring-loaded inlet check valve 3. As an another embodiment, the differential pressure generator 18 is provided between the fluid supply 7 and the inlet chamber 2, preferably in front of the first port 21 to generate a pressure difference across the separating member 61 when the fluid enters the inlet chamber 2.

According to the present disclosure, the backflow prevention device has simple structure, reduced dead space and small sizes and can work reliably.

While certain embodiments have been described, these embodiments have been presented by way of example only, and are not intended to limit the scope of the present disclosure. The attached claims and their equivalents are intended to cover all the modifications, substitutions and changes as would fall within the scope and spirit of the present disclosure.

The invention claimed is:

1. A backflow prevention device, comprising: an inlet chamber comprising at least two ports, in which a first port is used for receiving a fluid; a chamber-separating component comprising a separating member and a relief valve; an outlet chamber separated from the inlet chamber by the separating member and including a drain port and a fourth port; wherein the drain port is centrally formed in a bottom wall of the outlet chamber; and/or the drain port is fluidly connected with a funnel drainpipe for air gap separation; the relief valve being operatively connected with the separating member for opening or closing the drain port of the outlet chamber; wherein, when the relief valve is closed by means of a differential pressure applied on the separating member, the fluid is allowed to be delivered only from the fourth port of the outlet chamber.

2. The backflow prevention device according to claim 1, wherein a second port of the inlet chamber is fluidly connected with a spring-loaded inlet check valve that receives the fluid flowing across the inlet chamber and exiting from the second port.

3. The backflow prevention device according to claim 2, wherein the differential pressure is created by the spring-loaded inlet check valve which creates a pressure difference across the separating member when the fluid enters the inlet chamber.

4. The backflow prevention device according to claim 1, wherein a second port of the inlet chamber is fluidly connected with a differential pressure generator and an inlet check valve that receives the fluid flowing across the inlet chamber and exiting from the second port.

5. The backflow prevention device according to claim 4, wherein the differential pressure is created by the differential pressure generator which creates a pressure difference across the separating member when the fluid enters the inlet chamber.

6. The backflow prevention device according to any one of claim 2, wherein the inlet check valve is fluidly connected between the inlet chamber and the outlet chamber to only allow the fluid to flow from the inlet chamber toward the outlet chamber along a forward flowing path of the fluid.

7. The backflow prevention device according to claim 1, wherein the backflow prevention device further comprises: an outlet check valve being fluidly connected to the outlet chamber to only allow the fluid to flow through the outlet check valve for delivering the fluid from the outlet chamber.

8. The backflow prevention device according to claim 1, wherein the backflow prevention device further comprises: a drain port cleaning valve for rinsing and/or disinfecting the drain port, wherein the drain port cleaning valve is fluidly connected between the inlet chamber and the outlet chamber in parallel with either a spring-loaded inlet check valve or a combination of an inlet check valve and a differential pressure generator serially connected with the inlet check valve.

9. The backflow prevention device according to claim 8, wherein the drain port is used for draining the fluid in the outlet chamber as a backflow prevention measure when there is a leak in an inflow path to the outlet chamber and/or a leak in a delivering flow path from the outlet chamber.

10. The backflow prevention device according to claim 1, wherein the separating member is configured as a flexible membrane.

11. The backflow prevention device according to claim 1, wherein the chamber-separating component is supported by a support portion which extends inward radially from a corresponding inner wall of a housing of the backflow prevention device.

12. The backflow prevention device according to claim 1, wherein the relief valve is configured as a relief valve plunger connected with the separating member to form an integral assembly.

13. The backflow prevention device according to claim 12, wherein the assembly is supported by a spring which is supported on a bottom wall of the outlet chamber.

14. The backflow prevention device according to claim 1, wherein the backflow prevention device further comprises: an inflow detecting means for detecting a leak in the drain port when there is no fluid consumption delivered in a fourth port from the outlet chamber while there is fluid flowing through an inflow path to the outlet chamber.

15. The backflow prevention device according to any one of claim 1, wherein the inlet chamber is configured above the outlet chamber.

16. The backflow prevention device according to claim 1, wherein the outlet chamber has at least two ports, in which a third port is fluidly connected with an outlet of an inlet check valve fluidly disposed between the inlet chamber and the outlet chamber and a fourth port is fluidly connected with an inlet of an outlet check valve for delivering the fluid from the outlet chamber.

17. The backflow prevention device according to claim 12, wherein the relief valve plunger has a rod portion and a sealing head portion having a larger diameter compared with the rod portion.

18. The backflow prevention device according to claim 1, wherein at least portions of the backflow prevention device contacting the fluid are formed from a biocompatible material.

19. The backflow prevention device according to claim 15, wherein the inlet chamber and/or the outlet chamber has a cylindrical cavity whose height is smaller than its radius respectively.

20. A dialysis apparatus, wherein the dialysis apparatus comprises the backflow prevention device according to claim 1.

* * * * *

UNITED STATES PATENT AND TRADEMARK OFFICE
CERTIFICATE OF CORRECTION

| | |
|---|---|
| PATENT NO. | : 11,273,242 B2 |
| APPLICATION NO. | : 16/956329 |
| DATED | : March 15, 2022 |
| INVENTOR(S) | : Joseph Jor |

It is certified that error appears in the above-identified patent and that said Letters Patent is hereby corrected as shown below:

In the Claims

Column 7, Lines 59-60, in Claim 6, delete "according to any one of claim" and insert --according to claim--.

Column 8, Lines 40-41, in Claim 15, delete "according to any one of claim" and insert --according to claim--.

Signed and Sealed this
Thirteenth Day of June, 2023

Katherine Kelly Vidal
*Director of the United States Patent and Trademark Office*